United States Patent [19]
Wright et al.

[11] Patent Number: 5,860,955
[45] Date of Patent: Jan. 19, 1999

[54] LOCKING ANGIOPLASTY SYRINGE

[75] Inventors: Michael T. Wright, Quakertown; Kenneth C. Raines, Bethlehem, both of Pa.

[73] Assignee: B. Braun Medical Inc., Bethlehem, Pa.

[21] Appl. No.: 683,827

[22] Filed: Jul. 18, 1996

[51] Int. Cl.$^6$ .................................................. A61M 29/00
[52] U.S. Cl. ............................................... 604/99; 604/98
[58] Field of Search .................... 604/96, 99, 98

[56] References Cited

U.S. PATENT DOCUMENTS

| | | | |
|---|---|---|---|
| 4,655,749 | 4/1987 | Fischione | 604/98 |
| 4,758,223 | 7/1988 | Rydell | 604/98 |
| 5,047,015 | 9/1991 | Foote et al. | 604/99 |
| 5,284,480 | 2/1994 | Porter et al. | 604/99 |
| 5,318,534 | 6/1994 | Williams | 604/99 |
| 5,364,358 | 11/1994 | Hewitt et al. | 604/99 |
| 5,433,707 | 7/1995 | Call | 604/97 |
| 5,449,344 | 9/1995 | Taylor et al. | 604/99 |
| 5,472,424 | 12/1995 | Lampropoulos et al. | 604/99 |

*Primary Examiner*—Gary Jackson
*Attorney, Agent, or Firm*—Hopgood, Calimafde, Kalil & Judlowe

[57] ABSTRACT

A syringe includes a threaded plunger disposed for axial movement within a housing. When it is designed to aspirate a fluid into the syringe barrel, a cam member mounted on the barrel is moved to a free flow position in which it is disengaged from the plunger to allow the plunger to be freely axially movable along the barrel. When it is desired to inject the fluid, such as into an angioplasty balloon, the locking cam is moved to an engaged or locking position, in which it threadably engages the plunger, such that the plunger can only be moved along the barrel in small, controlled increments by rotating the plunger, thereby to enable the operator to achieve the desired accurate control over the fluid pressure in the syringe.

30 Claims, 4 Drawing Sheets

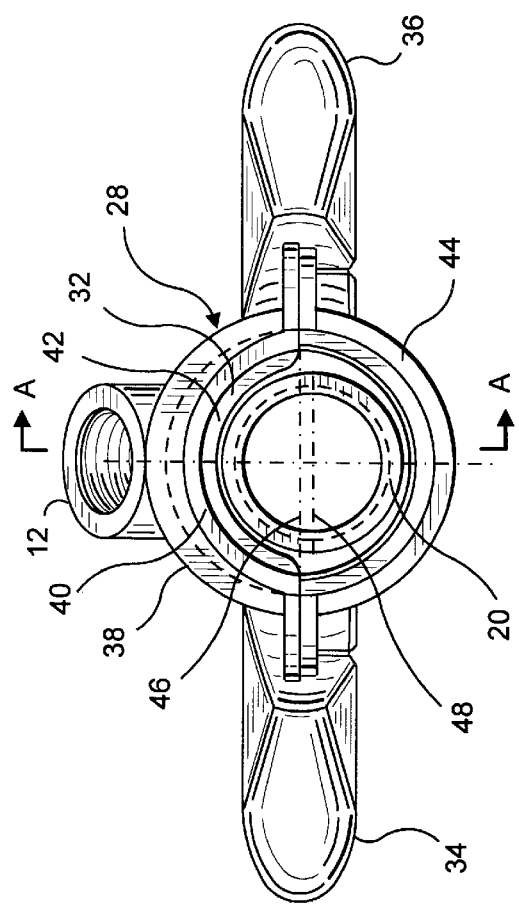
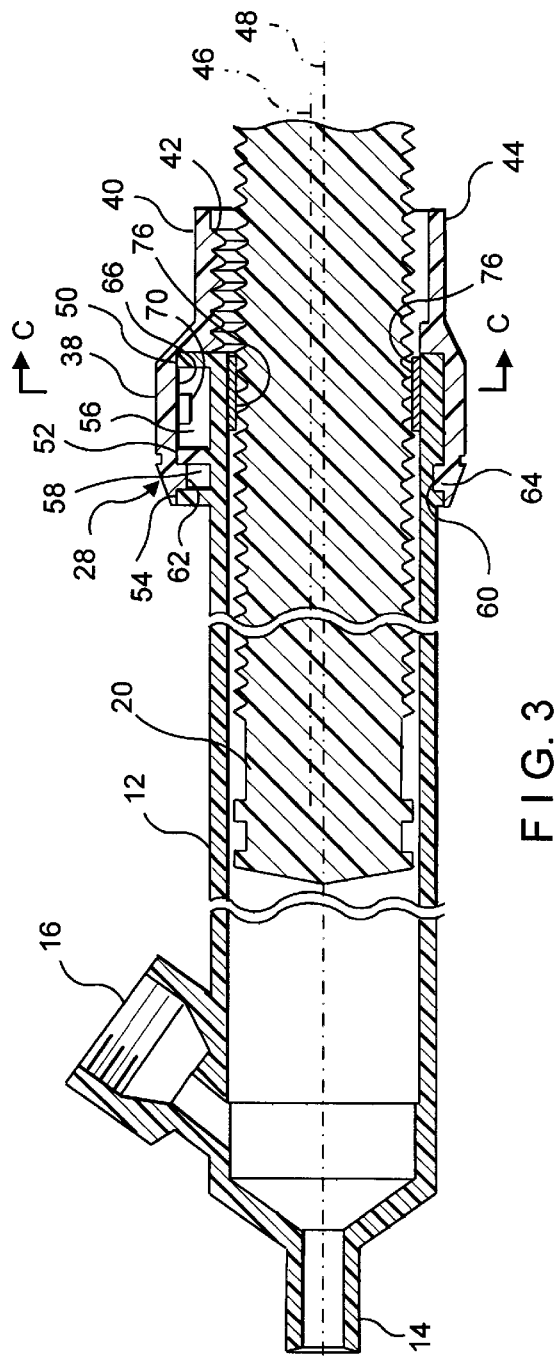
FIG. 2
FIG. 3

LOCKING ANGIOPLASTY SYRINGE

FIELD OF THE INVENTION

The present invention relates generally to syringes, and more particularly to a locking syringe for use in angioplasty and related procedures.

BACKGROUND OF THE INVENTION

Syringes have been commonly used for many years in medical applications to inject a fluid into a patient. In recent years, syringes have been used to inject a fluid into a patient's blood vessel in the performance of an angioplasty procedure, a relatively common procedure used to remove, or at least reduce, the amount of blockage typically caused by an accumulation of plaque that may have occurred in a blood vessel, commonly an artery.

In an angioplasty procedure, a balloon-tipped catheter or balloon is inserted into the artery involved in the procedure. Thereafter, a fluid is injected at an accurately controlled, relatively high pressure, in the order of 25–30 atmospheres, into the balloon or catheter to inflate the balloon. As the fluid fills the balloon, the latter inflates to fill the artery, thereby to compress the plaque in the artery. The physician then withdraws the fluid from the balloon causing the balloon to deflate, after which the catheter is removed from the patient.

A syringe is the preferred device used by physicians to introduce fluid into the balloon catheter. It has been found, as described in U.S. Pat No. 5,047,015, that in order to provide sufficient fluid pressure as well to achieve precise control over the fluid pressure, it is advantageous to employ a threaded plunger which can be freely, rapidly, axially reciprocated in a barrel, particularly when the balloon is being deflated. When greater control of fluid pressure, as well as a mechanical advantage to provide increased pressure, is desired, the threaded plunger engages mating threads on the interior surface of the barrel. When the plunger and barrel are thus threadably engaged, the syringe is locked, such that free, sliding, reciprocating movement of the plunger in the barrel is prevented. The plunger, however, in this condition or mode of operation can be screwed into, and thereby moved axially along the barrel in precisely controlled increments.

In the syringe described in the aforesaid U.S. Patent, transition of the syringe between the locked, threaded mode and the freely reciprocating mode of operation is achieved by the manual operation of an actuating trigger mechanism. Although this syringe is generally effective to achieve the desired high pressure and accurate control over the fluid pressure, the actuating trigger mechanism is relatively complex and is made up of a relatively large number of components, which adds to the overall cost of the syringe. There is thus a need for a syringe for use in angioplasty and related procedures that provides the precise control over the high fluid pressure required in such a procedure with a syringe that is less complex and less costly than those presently available.

BRIEF SUMMARY AND OBJECTS OF THE INVENTION

It is accordingly an object of the present invention to provide a syringe that can be selectively operated in either a freely reciprocating mode or in a threadably resistant or locked mode when greater precision of pressure control is desired.

It is a further object of the present invention to provide a syringe of the type described which is less complex and less costly than known syringes of this type.

It is another object of the present invention to provide a syringe of the type described in which transition of operation between the freely reciprocating mode to the locked, threadable mode can be achieved by the same hand that controls the operation of the plunger.

To these ends, the locking inflation syringe of the present invention includes a threaded plunger rod axially movable along a barrel. A threaded cam is positioned for relative rotation with respect to the barrel and plunger rod between a first, free flow position and a second, engaged position. In the engaged position, the cam and plunger rod are threadably engaged so that only restricted, but precisely controlled, axial movement of the plunger in the plunger is possible and the required high pressure up to 30 atmospheres can be is applied to the fluid in the barrel. When the cam is rotated into the free flow position, the plunger and cam are no longer engaged and the plunger can then be freely axially reciprocated along the barrel.

In a preferred embodiment of the invention, the cam is rotated along a raised circular surface formed at the proximal end of the barrel. The center line or axis of the barrel and plunger rod are axially colinear, whereas the axis of the cam is offset vertically from that of the barrel and plunger. A member on the cam engages a stop on the barrel to limit the angle of rotation of the cam with respect to the barrel to 90° between its two operating positions.

In a further aspect of the present invention, the rotary cam has two winged surfaces that can be engaged by the fingers of the hand that is used to move the plunger to cause rotation of the cam between its two operating positions. In a further aspect of the present invention, the mating threads on the plunger and cam are shaped to achieve easier engagement and to prevent unwanted relative movement between the cam and plunger even at high pressures. In yet a further aspect of the invention, a slit bushing is interposed between the plunger and barrel to prevent unwanted rocking of the plunger when it is in the locked or engaged mode, that is, after its threaded surface has become engaged with the threaded surface of the cam.

To the accomplishment of the above and such further objects as may hereinafter appear, the present invention relates to a locking syringe substantially as described in the appended claims, as considered with the following detailed description of a presently preferred embodiment of the invention and the accompanying drawings, in which:

BRIEF DESCRIPTION OF THE DRAWINGS

FIG. 2 is an end view of the locking syringe of FIG. 1 showing the rotatable cam in the free flow position;

FIG. 3 is a cross-sectional view taken along the plane A—A in FIG. 2;

DETAILED DESCRIPTION OF THE PREFERRED EMBODIMENT

Figure 1:
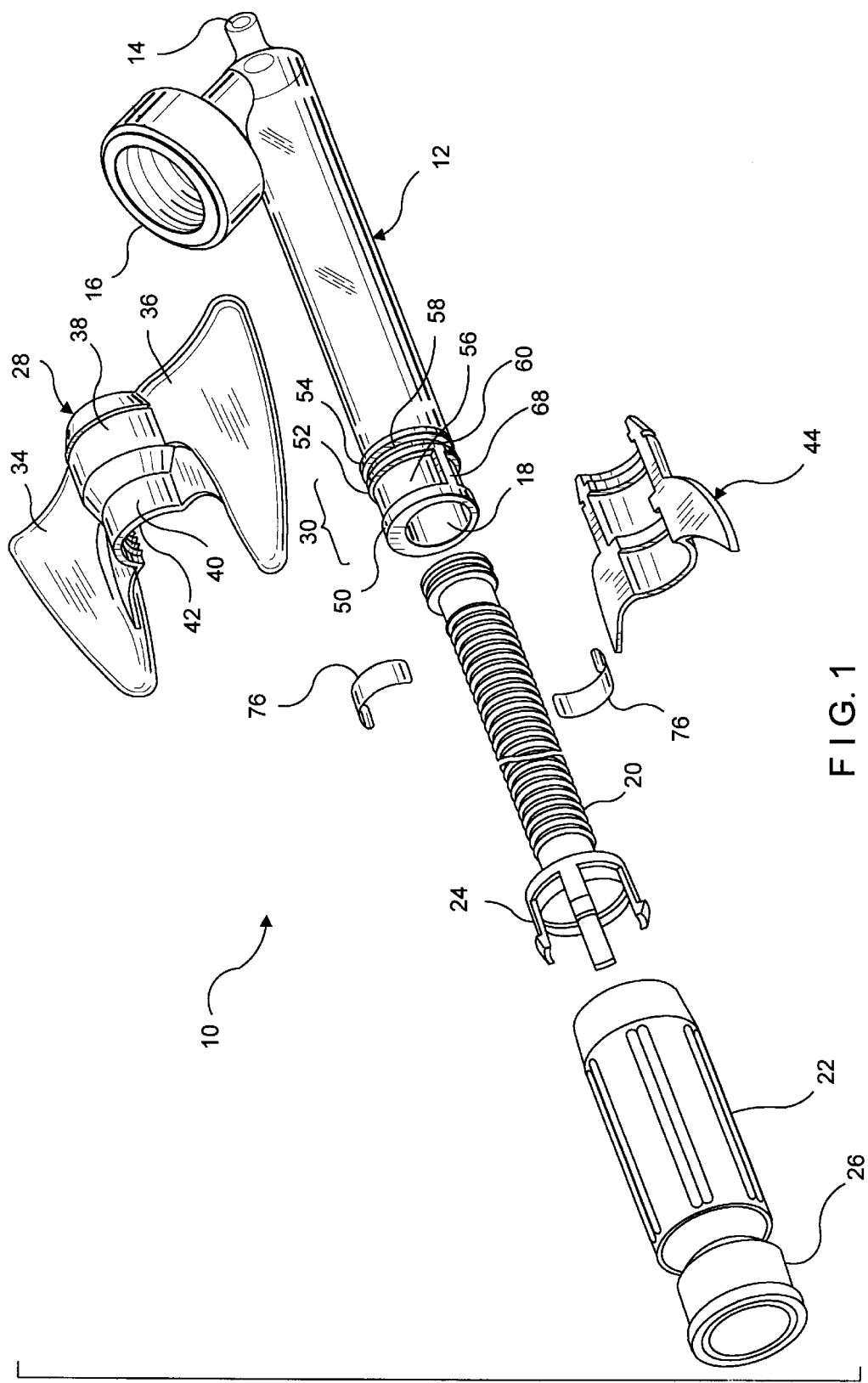
FIG. 1 is a perspective, exploded view of a locking syringe in accordance with an embodiment of the invention.

In accordance with a presently preferred embodiment of the invention, as illustrated in FIG. 1, a syringe apparatus generally designated 10 includes an elongated cylindrical barrel 12 for holding a fluid to be delivered or injected into a balloon or balloon catheter, such as in an angioplasty procedure. A narrow opening 14 is formed at the distal end of the barrel 12 through which the fluid may pass through a tube (not shown) to the balloon or catheter (also not shown). A pressure gauge 16 is mounted near the distal end of the barrel 12 to provide an indication of the pressure of the fluid leaving the syringe through the distal end of the barrel.

An opening 18 at the proximal end of barrel 12 receives the distal end of a plunger rod 20, which is threaded along most of its outer peripheral surface. A plunger knob 22 is placed over the proximal end of plunger rod 20 and is retained to the plunger rod by means of resilient fingers 24 secured to the proximal end of plunger rod 20 and received within the interior of plunger know 22. A knob plug 26 is secured to the proximal end of plunger knob 22 to facilitate the manipulation by the physician of the plunger knob and thus of the plunger rod, as described in more detail below.

In accordance with the present invention, plunger rod 20 can either be freely slid or reciprocated axially along and within the interior of the barrel 12, or when an accurately controlled high fluid pressure is required, it can be moved axially along the barrel in smaller, more precisely controlled axial increments. More particularly, in accordance with the invention a cam 28 is mounted for limited radiation about the barrel along a raised surface 30 formed near the proximal end of the barrel. As described in greater detail below, cam 28 can be rotated through an angle of 90° with respect to the plunger rod 20 between a first or free flow position in which the threaded surface on the cam is spaced from the plunger rod, to a second, engaged position in which the cam's threaded surface is brought into engagement with the threaded surface of the plunger rod. In the former, disengaged position, the plunger rod is freely axially movable along the barrel, whereas in the latter, engaged position of the cam, the plunger rod can no longer be freely axially moved along the barrel, but rather can only be rotated to cause it to move in precise small axial increments along the axial length of the barrel.

Figure 5:
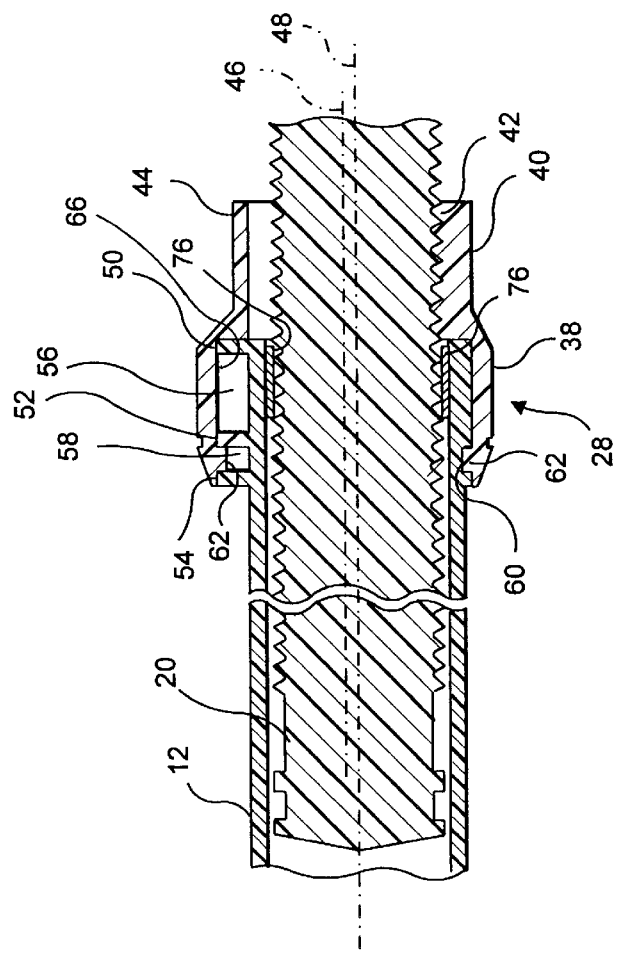
FIG. 5 is a partial cross-section taken along the plane B—B of FIG. 4.

Referring now to FIGS. 2–7, the cam 28 includes a semi-circular cam member 32 from which wings 34 and 36 extend in a radial, outward direction. Cam member 32 includes a large diameter section 38 and a contiguous, reduced-diameter section 40, the latter including an internal threaded section 42. A semicircular cam cap 44 is affixed to cam member 32 to form along with cam member 32 the cam 28. The large-diameter portion 38 and the corresponding portion of cam cap 44 are movably mounted about the proximal end of barrel 12 such that the narrower threaded section 42 of the cam 28, as shown in FIGS. 3 and 5, extends axially away from the end of the barrel and overlies a threadable portion of plunger rod 20. The centerline 46 of the winged cam cam-cap 28, when it is assembled and mounted on the barrel, is, as seen in FIGS. 2–7, vertically offset from the common centerline 48 of threaded plunger rod 20 and barrel 12.

The raised cam surface 30 may include, as shown, axially raised arcuate rail surfaces 50, 52, and 54 formed near the proximal end of an upper surface of barrel 12, as viewed in FIG. 3. The lower arcuate ends of surfaces 50, 52 and 54 are contiguous with the lower curved surface of the barrel, and they extend radially outwardly from the barrel at the opposite or upper surface of the barrel. Surfaces 50, 52 and 54 are preferably established by forming circular members each having a diameter greater than that of the barrel and having their centerlines vertically offset from that of the barrel.

Arcuate tracks or grooves 56 and 58 are established in the spaces between raised surfaces 50, 52 and 52, 54 respectively. An arcuate groove 60 is formed in the opposite surface of the barrel and is aligned with upper track 58. The large diameter section 38 of cam 28 includes an internal rail 62, which is received within groove 58, and an internal rib 64 on cam cap 44 is received in groove 60 on barrel 12. A rib or stop 68 (FIGS. 1, 6 and 7) extends axially between the circular surfaces 50 and 52. An internal wall 66 of cam member 32 abuts against arcuate surface 50. The engagement of an internal rib 70 on the cam section 38 and the stop 68 on the barrel (FIG. 7) limits further rotational movement of the cam with respect to the barrel.

Figure 4:
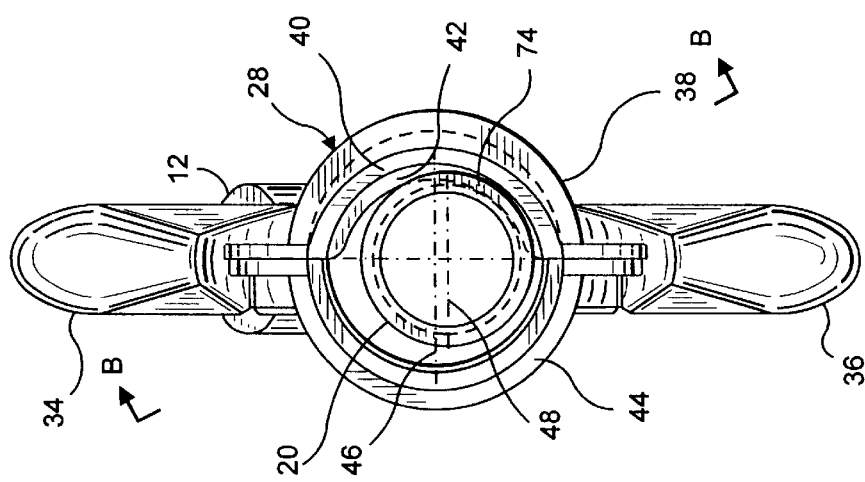
FIG. 4 is a view similar to FIG. 2 showing the cam in the engaged position.
Figure 7:
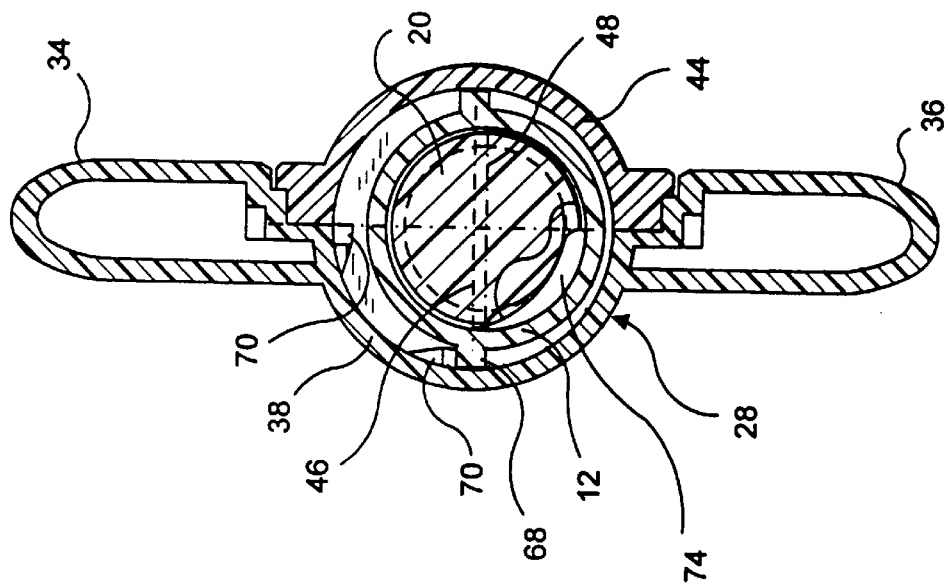
FIGS. 6 and 7 are cross-sectional views taken along plane C—C in FIG. 3, respectively showing the cam and plunger in the free-flow and engaged positions.
Figure 6:
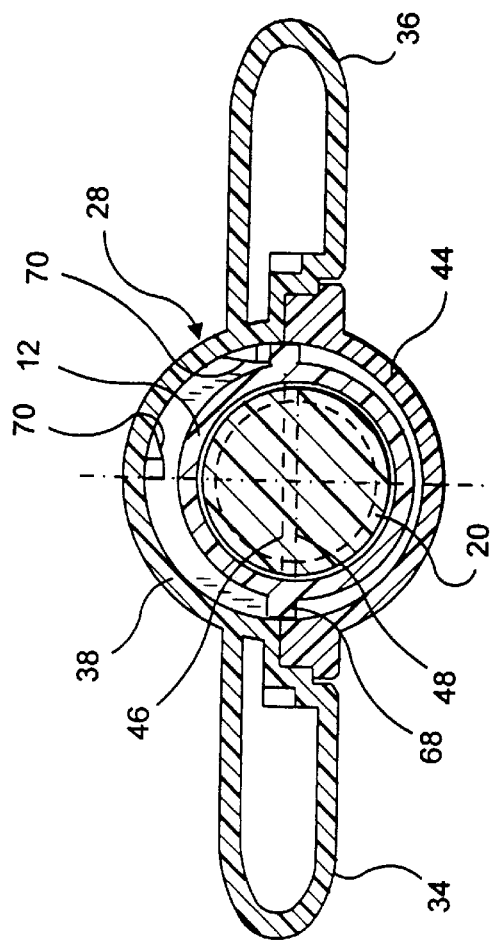

The cam 28 is thus mounted about the distal end of barrel 12 and is rotatable with respect to the barrel and plunger rod 20 by an angular displacement of 90° between a first or free flow position, shown in FIGS. 2, 3 and 6, in which the threaded surface 42 of the cam is spaced from the plunger and surface by the radial dimension of the raised arcuate surfaces 50, 52 and 54 and is thus disengaged from the threaded surface of the plunger rod, and a second or engaged portion, shown in FIGS. 4, 5 and 7 in which the threaded surface 42 of the cam is brought into engagement with the threaded plunger rod. The area of engagement of the cam threaded surface 42 and the threaded surface of plunger rod 20 is shown at 74 in FIGS. 4 and 7.

In the former or free flow position, the plunger rod can be moved or reciprocated freely axially along the barrel, whereas in the latter or engaged position, the plunger rod can only be moved in small, precise increments by turning or rotating the threaded plunger rod. As can best be seen in FIGS. 3 and 5, a pair of arcuate slit bushings 76 are disposed between the distal end of the barrel and the threaded surface of the plunger rod. The bushings 76 help to prevent radial movement or rocking of the plunger rod after it has been threadably engaged by the threaded cam surface 42 shown in FIG. 5. The mating teeth on the threaded cam surface 42 and those on the plunger rod 20 are preferably configured, as illustrated in FIGS. 3 and 5, as essentially a 45° right triangle with an arcuate tip. It has been found that this configuration further prevents undesired axial movement between the cam and plunger rod when the two are threadably engaged.

In operation, the end of a flexible connecting tube (not shown) affixed to the narrow end 14 of the barrel 12 is inserted into a container of a fluid to be injected from the syringe. For an angioplasty procedure in which the syringe is used to inflate and deflate a balloon the fluid would typically be a contact media. By engaging the wings 34, 36, with the thumb and forefinger of the hand that also controls the movement of the plunger, as described below, the cam 28 is then rotated to its free flow or disengaged position on the barrel, and the operator-physician then slowly and freely withdraws the plunger rod 20 to aspirate the desired volume, typically not more than 5 cc, of fluid into the distal end of the barrel. The operator then holds the syringe in an upright position and the plunger rod 20 is freely advanced axially along the barrel to eliminate any air that may have been introduced into the system during the aspiration of the fluid. After forming a meniscus of fluid on the dilation catheter inflation luer (not shown in the drawings), the narrow end 14 of the syringe is then connected to the balloon inflation port of the angioplasty catheter (also not shown).

To inflate the balloon, the winged cam is rotated 90° to its locked or engaged position, to threadably engage the cam and plunger rod, and the plunger rod 20 is slowly rotated by the fingers on the same hand used to rotate the winged cam in a clockwise direction, to cause the plunger rod to move axially in precisely controlled increments so as to increase fluid pressure, or in a counterclockwise direction to reduce fluid pressure. To deflate the balloon, the winged cam is rotated in the opposite direction to return it to its free flow or unlocked position, releasing the cam from its engagement with the plunger rod, which allows the plunger rod to be freely withdrawn from the barrel causing the fluid to be removed from the balloon.

It will be appreciated from the foregoing description of a presently preferred embodiment, that the present invention provides a locking syringe in which a change of operation from a freely axially moving plunger rod to restricted, high-pressure plunger rod movement is achieved in a reliable manner with a relatively inexpensive and less complex mechanism than was previously available. Moreover, although the syringe of the invention has been specifically described in the context of an angioplasty procedure, it may also be used to equal advantage in applications in which a balloon is inflated in other body lumens such as the bladder or urether. It will be also appreciated that modifications to the preferred embodiment can be made without necessarily departing from the spirit and scope of the invention.

What is claimed is:

1. A locking syringe comprising a barrel, a threaded plunger disposed in said barrel for axial movement therein, cam means movably mounted on said barrel for selectively controlling the freedom of axial movement of said plunger rod along said barrel, said cam means having a threaded surface and being movable with respect to said barrel from a first position in which said threaded surface of said cam means is disengaged from the threaded surface of said plunger rod to allow free axial movement of said plunger rod along said barrel, to a second position in which said threaded surface of said cam means engages the threaded surface of said plunger rod, thereby to restrict the freedom of axial movement of said plunger rod.

2. The locking syringe of claim 1, in which said barrel includes a raised arcuate surface along a portion of its periphery, said cam means being movable along said raised arcuate surface between its said first and second positions.

3. The locking syringe of claim 2, in which said arcuate surface includes at least first and second axially spaced circular members defining an arcuate groove therebetween, said cam means including an internal arcuate rail received in said groove.

4. The locking syringe of claim 2, in which said cam means is rotatable with respect to said barrel between said first and second positions and is spaced from said plunger rod by an amount equal to the radial extension of said arcuate surface from the surface of said barrel.

5. The locking syringe of claim 4, in which said cam means includes a pair of winglike members extending therefrom to enable said cam means to be manually moved between said first and second positions.

6. The locking syringe of claim 5, in which said cam means includes a large-radius section movably engaging said arcuate surface, and a reduced radius portion extending therefrom that includes said cam threaded surface.

7. The locking syringe of claim 6, further comprising cooperating means on said barrel and said cam means for limiting the rotational movement of said cam means between said first and second positions.

8. The locking syringe of claim 7, further comprising means interposed between said plunger rod and said barrel for further limiting radial movement of said plunger rod when said cam means is in its said second position.

9. The locking syringe of claim 8, in which the centerlines of said barrel and said plunger rod are essentially colinear and vertically offset from the centerline of said cam means.

10. The locking syringe of claim 9, in which said arcuate surface includes at least first and second axially spaced circular members defining an arcuate groove therebetween, said cam means including an internal arcuate rail received in said groove.

11. The locking syringe of claim 1, in which said cam means include a pair of winglike members extending therefrom to enable said cam means to be manually moved between said first and second positions.

12. The locking syringe of claim 11, in which said cam means includes a large-radius section movably engaging said arcuate surface, and a reduced radius portion extending therefrom that includes said cam threaded surface.

13. The locking syringe of claim 12, further comprising cooperating means on said barrel and said cam means for limiting the rotational movement of said cam means between said first and second positions.

14. The locking syringe of claim 13, further comprising means interposed between said plunger rod and said barrel for further limiting radial movement of said plunger rod when said cam means is in its said second position.

15. The locking syringe of claim 14, in which the centerlines of said barrel and said plunger rod are essentially colinear and vertically offset from the centerline of said cam means.

16. The locking syringe of claim 15, in which said arcuate surface includes at least first and second axially spaced circular members defining an arcuate groove therebetween, said cam means including an internal arcuate rail received in said groove.

17. The locking syringe of claim 1, in which said cam means includes a large-radius section movably engaging said arcuate surface, and a reduced radius portion extending therefrom that includes said cam threaded surface.

18. The locking syringe of claim 1, further comprising cooperating means on said barrel and said cam means for limiting the rotational movement of said cam means between said first and second positions.

19. The locking syringe of claim 1, further comprising means interposed between said plunger rod and said barrel for further limiting axial movement of said plunger rod when said cam means is in its said second position.

20. The locking syringe of claim 1, in which the centerlines of said barrel and said plunger rod are essentially colinear and vertically offset from the centerline of said cam means.

21. A pressure syringe for inflating and deflating a balloon catheter, said syringe comprising a barrel having a narrow distal end adapted to be operationally connected to a balloon catheter, a threaded plunger disposed within said barrel and axially movable within said barrel for injecting a fluid from said barrel to the balloon catheter at a controlled pressure, cam means mounted on the proximal end of said barrel for rotating movement with respect therewith, said cam means including a threaded surface and being rotatable with respect to said barrel between a first position in which it is spaced from said plunger, thereby permitting freely axial movement of said plunger within said barrel, to a second position in which said cam means threadably engages the threaded surface of said plunger, thereby restricting the axial movement of said plunger within said barrel.

22. The syringe of claim 21, in which said barrel includes a raised arcuate surface along a portion of its periphery, said cam means being movable along said raised arcuate surface between its said first and second positions.

23. The syringe of claim 22, in which said cam means is rotatable with respect to said barrel between said first and second positions and is spaced from said plunger by an amount equal to the radial extension of said arcuate surface from the surface of said barrel.

24. The syringe of claim 22, in which said cam means includes a large-radius section movably engaging said arcuate surface, and a reduced radius portion extending therefrom that includes said cam threaded surface.

25. The syringe of claim 22, in which said arcuate surface includes at least first and second axially spaced circular members defining an arcuate groove therebetween, said cam means including an internal arcuate rail received in said groove.

26. The syringe of claim 22, in which said cam means include a pair of winglike members extending therefrom to enable said cam means to be manually moved between said first and second positions.

27. The syringe of claim 21, in which said cam means include a pair of winglike members extending therefrom to enable said cam means to be manually moved between said first and second positions.

28. The syringe of claim 21, further comprising cooperating means on said barrel and said cam means for limiting the rotational movement of said cam means between said first and second positions.

29. The syringe of claim 21, further comprising means interposed between said plunger rod and said barrel for further limiting axial movement of said plunger when said cam means is in its said second position.

30. The syringe of claim 21, in which the colinear and vertically offset from the centerline of said cam means.

* * * * *